United States Patent [19]

Inazuka et al.

[11] 4,160,824
[45] Jul. 10, 1979

[54] INSECT ATTRACTIVE COMPOSITIONS

[75] Inventors: Shinichi Inazuka, Yokohama; Shigekatsu Tsuchiya, Yokosuka; Katsumi Suzuki, Tokyo; Toshiaki Miyanishi, Yokosuka, all of Japan

[73] Assignee: Ajinomoto Co., Inc., Tokyo, Japan

[21] Appl. No.: 893,815

[22] Filed: Apr. 5, 1978

Related U.S. Application Data

[63] Continuation of Ser. No. 714,126, Aug. 13, 1976, abandoned.

[30] Foreign Application Priority Data

Aug. 16, 1975 [JP] Japan .................................. 50/99077

[51] Int. Cl.$^2$ ...................... A01N 17/14; A01N 9/36; A01N 23/00
[52] U.S. Cl. .......................... 424/84; 426/1; 424/213
[58] Field of Search .............................. 424/84; 426/1

[56] References Cited

U.S. PATENT DOCUMENTS

| | | | |
|---|---|---|---|
| 3,391,001 | 7/1968 | Sair | 260/123.5 |
| 3,929,890 | 12/1975 | Pfister | 260/123.5 |
| 3,972,993 | 8/1976 | Kobayashi et al. | 424/84 |

OTHER PUBLICATIONS

*J. of Econ. Entomology*, Apr. 1959, pp. 279–285.
*J. of Econ. Entomology*, Aug. 1957, p. 505.
*J. of Econ. Entomology*, Apr. 1967, pp. 352–354.
*Food Industries*, Feb. 1948, pp. 118–120.

*Primary Examiner*—Donald B. Moyer
*Attorney, Agent, or Firm*—Oblon, Fisher, Spivak, McClelland & Maier

[57] ABSTRACT

Insect attractive compositions contain acid-hydrolyzed defatted cereals (protein hydrolysis percent $\geq 70\%$) which have been neutralized (pH 5 to 9), preferably, after being concentrated 2 to 10 times in strongly acidic media.

11 Claims, 5 Drawing Figures

INSECT ATTRACTIVE COMPOSITIONS

This is a continuation, of application Ser. No. 714,126, filed, Aug. 13, 1976, now abandoned.

BACKGROUND OF THE INVENTION

1. Field of the Invention

This invention is concerned with insect attractive compositions.

2. Description of the Prior Art

Thus far, insect attractants have been used with or without other drugs for the control of insects by means of surveying and monitoring of pest populations, mating disturbance, killing by luring with insecticide, attracting natural enemies of insects, etc. These are roughly classified into the food-type attractants and the other attractants (such as sex attractant). The former are, in particular, known to be widely effective against insect imagines irrespective of their sex, stage of emergence, or age, though its activity is extremely low as compared with that of a sex attractant. For example, acid-hydrolyzed (protein hydrolysis percent<70%) soy bean cakes (soy bean liquid) are used to control fruit flies but they are not effective enough because of their low activity to the insect.

SUMMARY OF THE INVENTION

After many efforts to overcome the shortcomings of acid-hydrolyzed soy bean cakes (soy bean liquid) which have been used so far, the present inventors have succeeded by finding that highly hydrolyzed (protein hydrolysis percent<70%) defatted cereals which have been neutralized, preferably, after being concentrated 2 to 10 times in strongly acidic media, are more greatly insect attractive than are the hydrolyzed soy bean cakes (soy bean liquid) (protein hydrolysis percent<70%) conventionally used as attractants. Moreover, it has been found that they are effective even for those insects which are hardly attracted by the soy bean cakes (soy bean liquid). The deffated cereals of this invention include those of soy bean, corn, cotton-seed, rape-seed, sesame, etc.

DETAILED DESCRIPTION OF THE PREFERRED EMBODIMENTS

The acid-hydrolysates used in this invention can be prepared by conventional methods. For instance, defatted cereals can be hydrolyzed with mineral acids such as sulfuric acid or hydrochloric acid and heat applied where necessary.

Determination of the protein hydrolysis percent is made by the well known Formol titration method and Kjedahl method which the Formol type nitrogen and the total nitrogen, respectively, to yield $$\text{protein hydrolysis percent} = \frac{\text{Formol type nitrogen}}{\text{total nitrogen}} \times 100$$

In order to prepare the insect attractive compositions of this invention from the hydrolysates thus obtained, impurities such as humus and inorganic substances are removed from the hydrolysates. More simply, the hydrolysates are, preferably, concentrated 2 to 10 times in acidic media (pH 4 to 7), more suitably 3 to 5 times, after being treated with an alkali such as NaOH, KOH, soda lime, ammonia, etc., and then neutralized to give a pH 5 to 9.

An example is given below for preparation of the insect attractive compositions.

One kilogram of defatted soy bean and 1.48 kilograms of hydrochloric acid (22%) are mixed and heated for 20 hrs at 115° C. with stirring. Humus is separated from the hydrolysate by filtration. The filtrate is concentrated 3 times by heating and neutralized with NaOH solution (20%) to make the pH of the solution 6.5. This way, about 3 kilograms of the product are obtained. The protein hydrolysis percent was 75.5% in this case.

The mixture obtained above can be used as is for an insect attractive composition of this invention. It can also be used as an insect attractive composition in the form of a solution, an emulsion, a wettable powder, a dust, granule, or an aerosol if it is dissolved or dispersed in a suitable liquid carrier (e.g., a solvent), or mixed with or adsorbed on a suitable solid carrier (e.g., a dust diluent and carrier), with the aid of an emulsifier, dispersing agent, suspending agent, spreading agent, penetrant, wetting agent, or stabilizing agent, where necessary.

Suitable solvents for the insect attractive compositions of this invention include water, alcohols (e.g., methyl alcohol, ethyl alcohol, ethylene glycol), ketones (e.g., acetone, methyl ethyl ketone), ethers (e.g., dioxane, tetra-hydrofuran, methyl cellosolve), aliphatic hydrocarbons (e.g., gasoline, kerosene, lamp oil), aromatic hydrocarbons (e.g., benzene, toluene, xylene, solvent naphtha), organic bases (e.g., pyridine), halogenated hydrocarbons (e.g., chloroform, carbon tetrachloride), acid amides (e.g., dimethyl formamide), esters (e.g., ethyl acetate, butyl acetate, fatty acid glycerides), nitriles (e.g., acetonitrile), and sulfur compounds (e.g., dimethyl sulfoxide). They are usually used alone or as mixtures of two or more components.

As dust diluents or carriers are used botanical powders (e.g., soy bean powder, tobacco powder, wheat flower, wood powder, etc.), mineral powders (e.g., clays like kaolinite, bentonite, and acid earth, talcs like phylite, silicas like diatom earth and mica), alumina, sulfur powder, and active charcoal. These powders can also be employed separately or as mixtures of two or more components.

Useful emulsifiers, spreading agents, and penetrants are soaps, sulfuric acid esters of higher alcohols, alkyl sulfonates, alkylaryl sulfonates, quarternary ammonium salts, fatty acid esters of oxyalkylamines, polyalkylene oxides, and sorbitols.

Where necessary, casein, gelatine, starch, alginic acid, agar, CMC, polyvinylalcohol, wood turpentine, rice-bran oil, sucrose, glucose, molasses, aminoacids, etc. can be added.

The insect attractive compositions of this invention can also be used with insecticides (chlorinated hydrocarbons, organic phosphorous compounds, carbamates, natural insecticides) synergic agents, other kinds of attractants, perfumes, germicides, etc.

The insect attractive compositions described above in detail are strongly insect-attractive and can be used with or without insecticides to survey, monitor, and control insect damage to human beings, animals, and plants. The acid-hydrolysates of proteins used in this invention are harmless to men and beasts.

They are effective against the insects of the classes Culicidae, Muscidae, Cecidomylidae, Trypetidae, Drosophilidae, Calliphoridae, Sarcophagidae, Agromyzidae, Tabanidae, etc.; of the classes Diptera, Blattidae, Blattellidae, etc.; of the classes Orthoptera, Myrmeleonidae of Heoroptera, Noctnidae, (*Adristyrannus amurensis Staudinger, Oraesia excavata Butler, Oraesia emarginata Fabricius, Heliothis assulta guenee, Prodenia litura Fabricius,* etc;) of the classes Lapidoptera, Yponomeutidae (e.g., *Plutilla maculipennis Curtis*), Carposinidae (e.g., *Carposina niponensia Walsingham*), Lymantrudae, etc.

EXAMPLE 1

A spherical insect attracting trap (McPhail trap) was fixed at the upper central part of a large-sized steel wire cage (200 cm×200 cm×200 cm).

Twenty five ml of a 1% sample solution (containing an insecticide) were placed in the trap. After allowing the system to stand for 24 hrs, the number of killed insects was counted.

The sample consisted of HCl-hydrolyzed defatted soy bean and corn cakes which were neutralized to give a pH of 5 with NaOH after being concentrated 3 times. The protein hydrolysis percentages had the values of 30, 40, 50, 60, 70, 80, and 90%. The total nitrogen was adjusted to 3.0 g/dl. The insects used were those of *Hylemyria platura Meigen, Chlorops oryzae Matsumura, Plutella xylosetella Linnaeus,* and *Culex pipiens pallens.* They were 1000 female imagines at the 4th day after emergence. The sample solution contained an insecticide (Sumithion). Table 1 gives the number of killed insects after a definite time. Larger number correspond to higher attractiveness. The table indicates clearly that all the samples made from highly hydrolyzed proteins (protein hydrolysis percent ≧ 70%) of defatted soy bean and corn cakes are strongly attractive to flies employed in this Example.

Table 2

| Sample | Conditions of concentration | Number of killed insects | Evaluation |
| --- | --- | --- | --- |
| 1 | Strongly acidic (pH < 3) | 71 | ++ |
| 2 | Weakly acidic or neutral (pH 5–7) | 5 | ± |
| 3 | Alkaline (pH = 8) | 3 | ± |
| 4 | Non-concentrated | 17 | + |

As is clear from Table 2, concentration of the hydrolysate at a strongly acidic pH gives a remarkable attractive effect on the insect. The same trend was found for other insects.

EXAMPLE 3

A mixture consisting of one part of HCl-hydrolysate of defatted soy been cake (protein hydrolysis percent=75%, neutralized with NaOH, total nitrogen=3 g/dl), one part of insecticide (DDVP:emulsifier= 1:1), and 98 parts of water was sprinkled over a paddy field. As a result, it was found that not only is the mixture very effective against the target insect but also it reduces the frequency of required sprinkling and raises the size of the rice crop as compared with a mixture of the same composition using a different HCl-hydrolysate of soy bean cake (protein hydrolisis percent=40%).

EXAMPLE 4

A mixture of ten parts of HCl-hydrolysate of defatted corn cake (protein hydrolysis percent=85%, neutralized with NaOH, total nitrogen=4.5 g/dl), 10 parts of Table 1

| | Protein hydrolysis percent | Acid decomposition-concentration of defatted soy bean | | | | Acid decomposition-concentration of defatted corn | | | |
| --- | --- | --- | --- | --- | --- | --- | --- | --- | --- |
| | | *Hylemyria Platula Meigen* | *Chlorops Oryzae Matsumura* | *Plutella Xylostella Linnaeus* | *Culex pipiens Pallens* | *Hylemyria Platula Meigen* | *Chlorops Oryzae Matsumura* | *Plutella Xylostella Linnaeus* | *Culex pipiens Pallens* |
| | 30% | 0 | 1 | 0 | 0 | 1 | 1 | 0 | 1 |
| Control | 40 | 1 | 2 | 1 | 2 | 1 | 1 | 2 | 1 |
| | 50 | 3 | 3 | 1 | 2 | 3 | 4 | 3 | 3 |
| | 60 | 4 | 2 | 3 | 3 | 4 | 2 | 6 | 3 |
| Present | 70 | 29 | 19 | 12 | 15 | 31 | 20 | 18 | 11 |
| Invention | 80 | 25 | 22 | 15 | 12 | 26 | 17 | 27 | 45 |
| | 90 | 23 | 18 | 12 | 17 | 25 | 14 | 30 | 29 | insecticide (MEP:emulsifier=1:1), 10 parts of crude sugar, 10 parts of alginic acid, and 60 parts of water was sprinkled over a peach orchard. This mixture was found to kill the target insects (e.g. peach fruit moth) effectively and reduce damage from the insects drastically.

EXAMPLE 2

One kilogram of defatted soy bean and 1.48 kilograms of hydrochloric acid (22%) were mixed and heated for 20 hrs at 115° C. with stirring. Humus was then separated from the reaction mixture by filtration. The filtrate was concentrated 3 times under the conditions indicated in Table 2. The pH of the solution was brought to 6.7 by adding an alkali. By using the sample thus prepared attractive tests were performed on *Musca domestica Linner* flies. The results obtained are given in Table 2. The insects used were 1000 female imagines of *Musca domestica Linner* at the 4th day after emergency. The method of testing was the same as that adopted in Example 1. Data were taken in duplicate 48 hrs after the start of the test and averaged.

EXAMPLE 5

A McPhail trap shown in FIG. 2 was hung down from the ceiling of a trap type olfactometer depicted in FIG. 1. The olfactometer was a plastic box (100 cm×100 cm×100 cm) and had a steel wire cover on the top. A motor was fixed at the center of the ceiling of the olfactometer to rotate the hanger to which the trap is attached as shown in FIG. 3. At the center of the bottom of the olfactometer a dish and a pot were placed. They contained some cubes of sugar and water, respectively, as baits for the target insects. A tangle food was applied on the legs of the olfactometer.

The target insects were 100 each of male and female melon flies at the 3rd day after emergency. Each of the traps contained 20 ml each of the samples A to C, below, and was rotated at a constant speed of 1/15 r.p.m. The number of killed insects in each olfactometer was counted over 17 hrs from 5 p.m. to 10 a.m.

The results obtained are given in FIGS. 4 and 5, which indicate that the hydrolysates of soy bean protein and cotton seed protein are strongly insect-attractive at pH higher than 5 if they have been hydrolyzed and concentrated to give the same protein hydrolysis percent and the same concentration.

| Sample | Content |
|---|---|
| A | Insecticide alone (Malathion emulsion) 1000 times diluted |
| B | Soy bean protein hydrolysate (protein hydrolysis percent = 70%, 3 times concentrated, pH = 1.0-9.0, total nitrogen = 3.0 g/dl)     10 parts<br>Insecticide (Malathion emulsion) 1 part 1000 times diluted |
| C | Cotton seed protein hydrolysate (protein hydrolysis percent = 75%, 3 times concentrated, pH = 1.0-9.0, total nitrogen = 3.0 g/dl)    10 parts<br>Insecticide (Malathion emulsion) 1 part 100 times diluted |

EXAMPLE 6

A field test was carried out at Ishiki, Itoman City, Okinawa Prefecture (Southern part of Okinawa Island), Japan. Traps of the type shown in FIG. 2 were hung from branches of trees and 100 ml of the sample solutions were sprinkled with a hand spray on the surface of the leaves of the trees right above the traps. Next day, the numbers of killed Melon flies and Oriental fruit flies were counted.

The samples used were as follows.

D  Insecticide (Malathion emulsion), 1000 times diluted.
E  { Commercially available acid-hydrolysate of plant proteins*
      Insecticide (Malathion emulsion) 10 parts
      100 times diluted  1 part
*"PIB7" ® (A product of Staley Co., Ltd., U.S.A., Protein hydrolysis %: 47%)
F  { Commercially available acid-hydrolyzed soy bean proteins*
      Insecticide 10 parts
      100 times diluted  1 part
*"Nasiman" ® (A product of Israel)
G  { Acid-hydrolysate of soy bean proteins 10 parts
      (Protein hydrolysis percent: 40 and 70%, 3 times concentrated, pH 6.5, total nitrogen: 3.0 g/dl)
      Insecticide (Malathion emulsion) 1 part
      100 times diluted
H  { Acid-hydrolysate of corn proteins 10 parts
      (Protein hydrolysis percent: 40 and 70%, 3 times concentrated, pH 6.5, total nitrogen 3.0 g/dl)
      Insecticide (Malathion emulsion) 1 part
      100 times diluted The results of the above field test are summarized in Table 3, in which the hydrolysates in this device show a high activity.

Table 3

| Sample | Protein hydrolysis percent | PH | Number of attracted flies |||||||
|---|---|---|---|---|---|---|---|---|
| | | | Melon fly ||| Oriental fruit fly |||
| | | | ♀ | ♂ | ♀ + ♂ | ♀ | ♂ | ♀ + ♂ |
| D | — | — | 0 | 0 | 0 | 0 | 0 | 0 |
| E | 47% | 4.8 | 1.0 ± 1.0 | 2.0 ± 1.0 | 3.0 ± 2.0 | 0.5 ± 0.5 | 1.0 ± 1.0 | 1.5 ± 1.5 |
| F | 65.5 | 4.39 | 1.0 ± 1.0 | 1.0 ± 1.0 | 2.0 ± 2.0 | 0.5 ± 0.5 | 2.0 ± 1.0 | 2.5 ± 0.5 |
| G | 40 | 6.5 | 2.0 ± 1.0 | 2.0 ± 0 | 4.0 ± 1.0 | 2.0 ± 1.0 | 1.0 ± 1.0 | 3.0 ± 2.0 |
| " | 70 | 6.5 | 7.5 ± 0.5 | 4.5 ± 1.5 | 12.0 ± 1.0 | 5.5 ± 1.5 | 6.0 ± 1.0 | 11.5 ± 2.5 |
| H | 40 | 6.5 | 2.0 ± 1.0 | 2.0 ± 1.0 | 4.0 ± 2.0 | 2.0 ± 2.0 | 2.0 ± 1.0 | 4.0 ± 1.0 |
| " | 70 | 6.5 | 10.5 ± 2.5 | 5.0 ± 2.0 | 15.5 ± 4.5 | 8.5 ± 1.5 | 4.0 ± 1.0 | 12.5 ± 2.5 |

EXAMPLE 7

An indoor test was performed using the same apparatus as in Example 5. The trap was rotated at a constant rate of 1/15 r.p.m. After a definite period of time, the number of killed flies in the trap was counted.

Testing period: 17 hrs from 5 p.m. to 10 a.m.

| Target flies | |
|---|---|
| (1) Melon flies | 100 each of male and female insects at the 3rd day after emergency |
| (2) Oriental fruit flies | 100 each of male and female insects at the 3rd day after emergency |
| Baits for the flies | Cubes of sugar and water |
| Sample solutions | 20 ml each of the samples I to L were placed in McPhail traps |

I  Insecticide (Malathion emulsion) alone, 1000 times diluted
J  { Commercially available acid-hydrolysate of soy bean proteins                        10 parts
     "PIB-7" ® (A product of A.E. Staley Co., Ltd., U.S.A.,
     Protein hydrolysis percent: 47%, pH 4.8)
     Insecticide (Malathion emulsion)             1 part
     100 times diluted
K  { Acid-hydrolysate of soy bean proteins       10 parts
     (Protein hydrolysis percent: 20-90%, 3 times concentrated
     pH 6.5. total nitrogen 3.0 g/dl)
     Insecticide (Malathion emulsion)              1 part
     100 times diluted
L  { Acid-hydrolysate of corn proteins            10 parts
     (Protein hydrolysis percent: 20-90%, 3 times concentrated
     pH 6.5, total nitrogen 3.0 g/dl)
     Insecticide (Malathion emulsion)              1 part
     100 times diluted The results of the test are given in Table 4.

Insect-attractiveness index =
Average of $\dfrac{\text{Number of lured insects by one of the samples}}{\text{Number of lured insects by "PIB-7"}}$ The higher the index is, the higher is the activity. As is indicated in Table 4, the activity of the acid-hydrolysates of soy bean proteins and corn proteins increases remarkably when their protein hydrolysis percent exceeds 70%.

Table 4

| | Sample | Protein hydrolysis percent | PH | Insect-attractiveness index | | | | | |
|---|---|---|---|---|---|---|---|---|---|
| | | | | Melon fly | | | Oriental fruit fly | | |
| | | | | ♀ | ♂ | ♀ + ♂ | ♀ | ♂ | ♀ + ♂ |
| Control | I | — | — | 0 | 0.2 | 0.1 | 0 | 0.5 | 0.3 |
| | J | 47 | 4.8 | 1.0 | 1.0 | 1.0 | 1.0 | 1.0 | 1.0 |
| | K | 20 | 6.5 | 0.8 | 0.5 | 0.7 | 1.0 | 0.8 | 0.9 |
| | | 40 | 6.5 | 1.2 | 1.5 | 1.3 | 1.4 | 1.7 | 1.6 |
| | | 60 | 6.5 | 2.0 | 1.8 | 1.9 | 1.8 | 1.5 | 1.6 |
| | L | 20 | 6.5 | 0.5 | 0.9 | 0.7 | 0.8 | 1.5 | 1.3 |
| | | 40 | 6.5 | 1.5 | 2.4 | 1.9 | 1.6 | 0.9 | 1.1 |
| | | 60 | 6.5 | 2.2 | 2.0 | 2.1 | 2.0 | 1.0 | 1.3 |
| Present Invention | K | 70 | 6.5 | 4.8 | 5.0 | 4.9 | 3.9 | 2.0 | 2.6 |
| | | 90 | 6.5 | 4.7 | 5.3 | 5.0 | 4.5 | 3.0 | 3.5 |
| | L | 70 | 6.5 | 5.3 | 6.2 | 5.7 | 4.0 | 1.4 | 2.3 |
| | | 90 | 6.5 | 5.0 | 7.0 | 5.9 | 4.3 | 1.2 | 2.2 |

The results of a comparative test using commerciably available "PIB-7" (U.S.A.), "Nasiman" (Israel), and a sample in this invention are shown in Table 5.

Table 5

| | | "PIB-7" ® | "Nasiman" ® | Product of this invention* |
|---|---|---|---|---|
| pH | | 4.80 | 4.39 | 6.50 |
| NaCl | | 12.63 g/dl | 14.34 g/dl | 15.0 g/dl |
| Total N | | 3.79 | 2.96 | 4.87 |
| $NH_3$ form N | | 0.49 | 0.68 | 0.60 |
| Formol form N | | 1.79 | 1.94 | 3.61 |
| Protein hydrolysis percent | | 47.2% | unknown | 74.0 % |
| Amino Acid | Lys HCl | 679 mg/dl | 547 mg/dl | 2,271 mg/dl |
| | His HCl | 282 | 309 | 1,025 |
| | Arg HCl | 806 | 694 | 1,986 |
| | Asp | 998 | 1,034 | 3,481 |
| | Threo | 522 | 453 | 1,139 |
| | Serine | 976 | 853 | 1,590 |
| | Glu | 1,127 | 4,216 | 5,865 |
| | Pro | 1,641 | 1,953 | 1,696 |
| | Gly | 382 | 624 | 1,143 |
| | Ala | 1,584 | 612 | 1,526 |
| | Cys H | (+) | (+) | (+) |
| | Val | 562 | 499 | 1,212 |
| | Met | 236 | 31 | 273 |
| | I Leu | 238 | 385 | 1,259 |
| | Leu | 910 | 1,023 | 2,865 |
| | Tyr | 162 | 125 | 582 |
| | Phe | 669 | 584 | 1,513 |
| | Total | 11,174 | 13,942 | 29,426 |
| Organic Acid | PCA | 2,011 | | 224 |
| | Lact | 3,273 | | 382 |
| | Acet | 198 | | 134 |
| | Lev | 987 | | 4,675 |
| | Form | 362 | | 631 |
| | Cit | 185 | | 2,049 |
| | Succ | 50 | | 78 |

Figure 1:
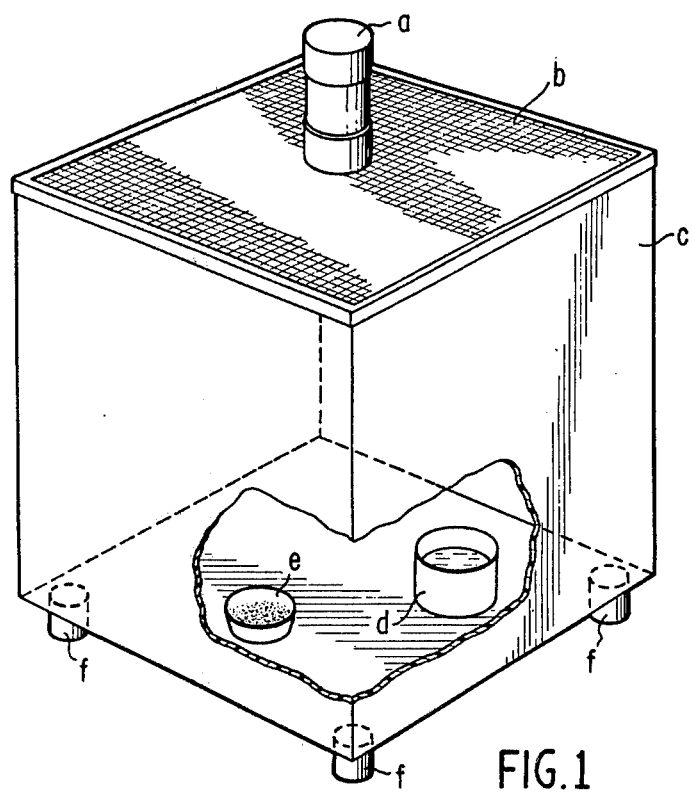
FIGS. 1, 2, and 3 show respectively a trap type olfactometer, a McPhail trap, and rotation of the trap. Here, (a) is a motor, (b) a steel wire cover, (c) a plastic box, (d) a water pot, (e) a sugar dish, (f) legs, (g) sample, (h) a McPhail trap, (i) a hanger, and (j) a motor.
Figures 2, 3:
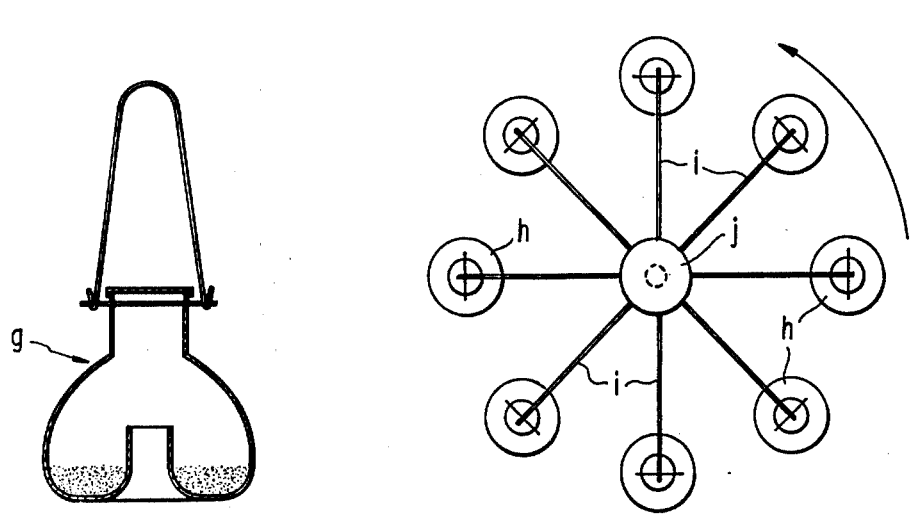
Figure 4:
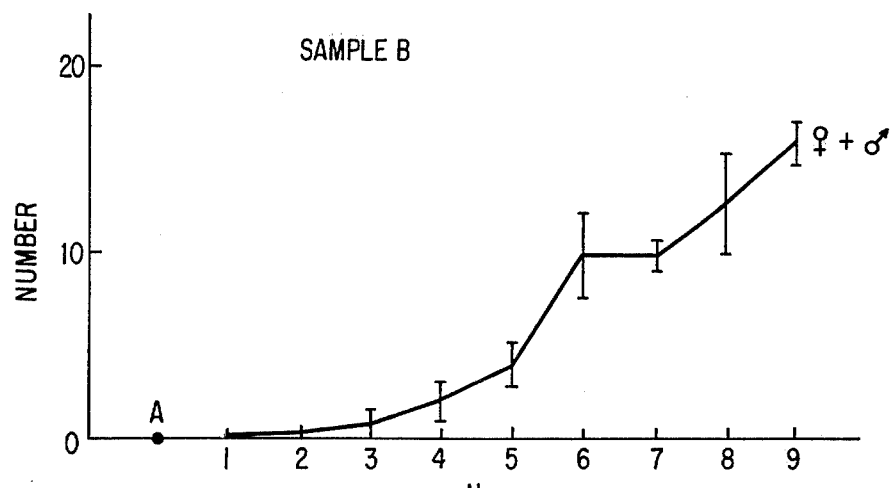
FIGS. 4 and 5 give the results obtained in Example 5 using the samples B and C.
Figure 5:
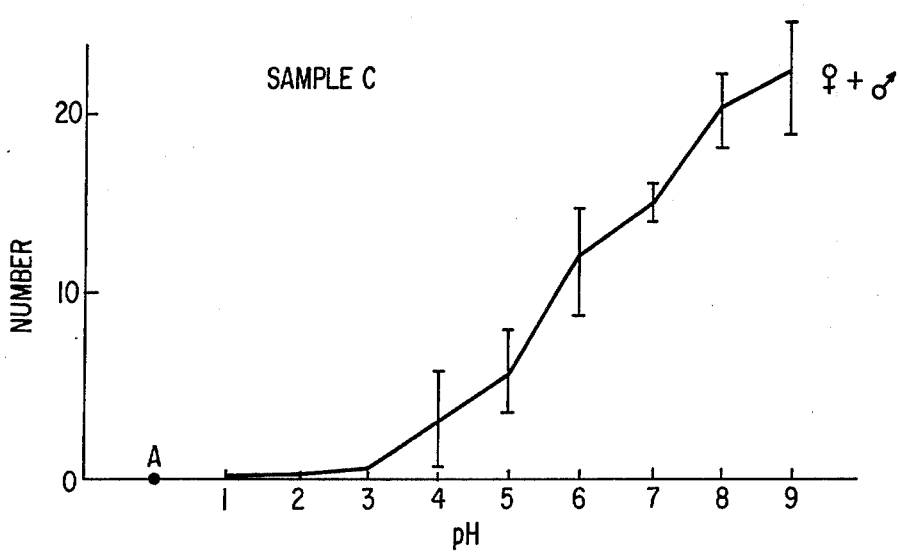

What is claimed is:

1. In an insect attractive and killing composition which comprises a vegetable protein hydrolysate and an insecticide, the improvement wherein said protein hydrolysate is an acid-hydrolyzed defatted vegetable protein having a protein hydrolysis percent ≧70%, which has been neutralized to a pH of 5-9.

2. The insect attractant composition of claim 1 wherein said acid-hydrolyzed defatted vegetable protein is derived from at least one member selected from the group consisting of soy beans, corn, cotton seed, and rape seed.

3. A method of killing insects which comprises exposing said insects to the insect attractive and killing composition of claim 1.

4. In a method of killing oriental fruit flies comprising exposing said fruit flies to an insect attractive and killing composition comprising a hydrolyzed vegetable protein and an insecticide, the improvement wherein said hydrolyzed protein is the acid-hydrolyzed vegetable protein of claim 1, wherein the vegetable protein is selected from the group consisting of soy bean protein and corn protein.

5. In an insect attractive composition which comprises a vegetable protein hydrolysate, the improvement wherein said protein hydrolysate is an acid-hydrolyzed defatted vegetable protein having a protein hydrolysis percent ≧70%, which has been concentrated 2-10 times in a strongly acidic medium, and thereafter has been neutralized to a pH of 5-9.

6. The composition of claim 5, which further comprises an insecticide.

7. The method of killing insects which comprises exposing the insects to the insect attractive composition of claim 6.

8. The insect attractive composition of claim 5 wherein said vegetable protein is derived from at least one member selected from the group consisting of soy beans, corn, cotton seed and rape seed.

9. The method of attracting insects which comprises exposing the insects to the insect attractive composition of claim 5.

10. In a method of attracting oriental fruit flies comprising exposing said flies to an insect attractive composition comprising a hydrolyzed vegetable protein, the improvement wherein said hydrolyzed protein is the acid-hydrolyzed vegetable protein of claim 5 wherein the vegetable protein is selected from the group consisting of soy bean protein and corn protein.

11. In a method of killing oriental fruit flies comprising exposing said flies to an insect attractant and killing composition comprising a hydrolyzed vegetable protein and an insecticide, the improvement wherein said hydrolyzed protein is the acid-hydrolyzed protein of claim 5 wherein the vegetable protein is selected from the group consisting of soy bean and corn protein.

* * * * *